United States Patent
Ho

(10) Patent No.: US 7,303,763 B2
(45) Date of Patent: *Dec. 4, 2007

(54) COMPOSITIONS FOR CONJUGATED ESTROGENS AND ASSOCIATED METHODS

(75) Inventor: Thomas Ho, Irvine, CA (US)

(73) Assignee: Watson Laboratories, Inc., Salt Lake City, UT (US)

( * ) Notice: Subject to any disclaimer, the term of this patent is extended or adjusted under 35 U.S.C. 154(b) by 784 days.

This patent is subject to a terminal disclaimer.

(21) Appl. No.: 10/668,104

(22) Filed: Sep. 22, 2003

(65) Prior Publication Data

US 2004/0131683 A1 Jul. 8, 2004

Related U.S. Application Data

(63) Continuation-in-part of application No. 10/076,046, filed on Feb. 12, 2002, now Pat. No. 6,630,166.

(60) Provisional application No. 60/268,177, filed on Feb. 12, 2001.

(51) Int. Cl.
*A61K 9/36* (2006.01)
*A61K 9/28* (2006.01)
*A61K 9/30* (2006.01)
*A61K 9/32* (2006.01)

(52) U.S. Cl. ............... 424/479; 424/474; 424/475; 424/482

(58) Field of Classification Search ........... 424/474, 424/475, 479, 482
See application file for complete search history.

(56) References Cited

U.S. PATENT DOCUMENTS

| 2,565,115 | A |   | 8/1951 | Bates et al. |
| 2,720,483 | A |   | 10/1955 | Stiller et al. |
| 4,309,405 | A |   | 1/1982 | Guley et al. |
| 5,395,627 | A |   | 3/1995 | Dopper et al. |
| 5,547,948 | A | * | 8/1996 | Barcomb |
| 5,720,977 | A |   | 2/1998 | Deghenghi |
| 5,908,638 | A | * | 6/1999 | Huber et al. |
| 6,346,269 | B1 | * | 2/2002 | Hsiao et al. |
| 6,630,166 | B1 |   | 10/2003 | Ho |

* cited by examiner

*Primary Examiner*—Humera N Sheikh
(74) *Attorney, Agent, or Firm*—Thorpe North & Western, LLP

(57) ABSTRACT

Oral conjugated estrogen formulations are disclosed and described. In one aspect, the oral formulation may be a tablet having a core and one or more coatings thereon. In addition to conjugated estrogen ingredients, the core may include one or more organic excipients and one or more inorganic excipients. In one aspect, the organic excipients may include less than about 20% w/w of a cellulose ingredient, and less than about 50% w/w of a sugar ingredient. In another aspect, the inorganic excipients may include less than about 10% w/w of a calcium phosphate tribasic ingredient. In yet another aspect, the formulation does not crack when stored at about 40° C. and about 75% relative humidity for about 2 months.

22 Claims, 2 Drawing Sheets

US 7,303,763 B2

COMPOSITIONS FOR CONJUGATED ESTROGENS AND ASSOCIATED METHODS

PRIORITY DATA

This application is a continuation-in-part of U.S. patent application Ser. No. 10/076,046, filed on Feb. 12, 2002 now U.S. Pat. No. 6,630,166, which claims priority to U.S. Provisional Patent application Ser. No. 60/268,177, filed on Feb. 12, 2001, each of which are incorporated herein by reference.

FIELD OF THE INVENTION

The present invention relates generally to conjugated estrogen formulations and methods of administering such compositions. Accordingly, this invention covers the fields of pharmaceutical sciences, medicine, cosmetics, and related sciences.

BACKGROUND OF THE INVENTION

Conjugated estrogens have been used for years as an estrogen supplement in order to treat or prevent a variety of conditions that are induced or exacerbated by estrogen hormone deficiency. Particularly, conditions experienced by peri-menopausal, menopausal, and post-menopausal women such as osteoporosis, hot flashes, vaginal atrophy, and loss of protection against heart attacks, can be ameliorated using conjugated estrogens as part of an estrogen replacement therapy routine.

Although conjugated estrogens may be administered using various routes of administration, oral tablet administration has traditionally been the most common. Such formulations have not only contained conjugated estrogens, but have also included other hormones, such as progesterone in order to balance the physiological effects of estrogen supplementation. For example, oral estrogen replacement tablets containing either a conjugated estrogen, or combination of conjugated estrogen and medroxyprogesterone acetate are currently marketed under the trade names PREMARIN®, PREMPRO™, and PREMPHASE®, by Wyeth-Ayerst Laboratories, Inc.

While oral tablet regimens of conjugated estrogen have been able to achieve acceptable therapeutic results, various drawbacks to known oral tablet formulations still exist. Example of such drawbacks include erratic drug release, degradation of the conjugated estrogen, and cracking of the tablet formulation during storage.

A variety oral tablet formulations of both instant and sustained release for administering conjugated estrogen are currently known. For example, U.S. Pat. No. 5,395,627, which is incorporated herein by reference in its entirety, discloses pharmaceutical granulates and process for making granulates to be used in oral tablet manufacture, which are very resistant to segregation, and which display an increased stability for certain steroids, such as estrogens and progestogens.

U.S. Pat. No. 5,547,948, which is incorporated herein by reference in its entirety, discloses a sugar coating composition for application to a compressed medicinal tablet used to co-deliver two or more pharmacologically-active agents. Particularly, the sugar coating composition includes sugar, a therapeutic amount of a hormonal steroid, and a hormonal steroid release-controlling amount of microcrystalline cellulose. The tablet core contains a medicinal agent which is conventionally co-delivered with the specific steroid in the sugar coating.

U.S. Pat. No. 5,720,977, which is incorporated herein by reference in its entirety, discloses an effervescent oral formulation containing a water-soluble and stable estrogen compound, such as estropipate, or estrone, a water soluble calcium salt, and a pharmaceutically acceptable excipient. The effervescent activity of the tablet is purported to aid the body's absorption of estrone and other estrogens due to their water insoluble nature. Further, the calcium component of the effervescent causing ingredients may be used as a calcium supplement to further protect against bone loss and osteoporosis.

U.S. Pat. No. 5,908,638, which is incorporated herein by reference in its entirety, discloses a solid dosage unit form containing low dose conjugated estrogens that are released at regular increments (i.e. sustained release) upon oral administration. Generally, the sustained release of estrogens and other hormones, when included, is accomplished by the inclusion of a high molecular weight hydroxypropylmethylcellulose, which may be further combined with other hydrophilic gums. In addition to controlled release, this patent discloses that strict control of moisture content within the formulation is essential to stabilizing conjugated estrogens and achieving a uniform release thereof.

In spite of the foregoing, problems such as insolubility, instability, and tablet cracking associated with oral conjugated estrogen tablets still persist. Therefore, an oral tablet formulation which overcomes, or at least ameliorates, these shortcomings continues to be sought through ongoing research and development efforts.

SUMMARY OF THE INVENTION

Accordingly, the present invention provides a pharmaceutical composition in a solid oral dosage form which does not crack after storage at about 40°C. and about 75% relative humidity for about 2 months. In other words, the compositions are stable under ambient conditions in most environments. In one aspect, the solid oral dosage form may be a tablet having a core containing a therapeutically effective amount of a conjugated estrogen, or a hormonal component thereof, at least one organic excipient, at least one inorganic excipient. A variety of specific conjugated estrogens and specific amounts thereof may be included. However, in one aspect, the conjugated estrogen may be present in an amount of from about 0.1 mg to about 3 mg. In another aspect, the amount may be about 0.625 mg.

A variety of organic excipients may be used in the core of the present oral formulation. In one aspect, the organic excipients may include less than about 25% w/w of a cellulose ingredient, and less than 50% w/w of a sugar ingredient. Further, while a variety of inorganic excipients may be used, in one aspect, the inorganic excipients may include less than about 10% w/w of a calcium phosphate tribasic ingredient.

In addition to the core recited above, the oral formulation of the present invention may include an outer coating. In one aspect, the coating may be substantially free of hormones. In another aspect, the coating may contain one or more sugar ingredients. In yet another aspect, the coating may include one or more acrylic polymers.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

DETAILED DESCRIPTION

Figure 1:
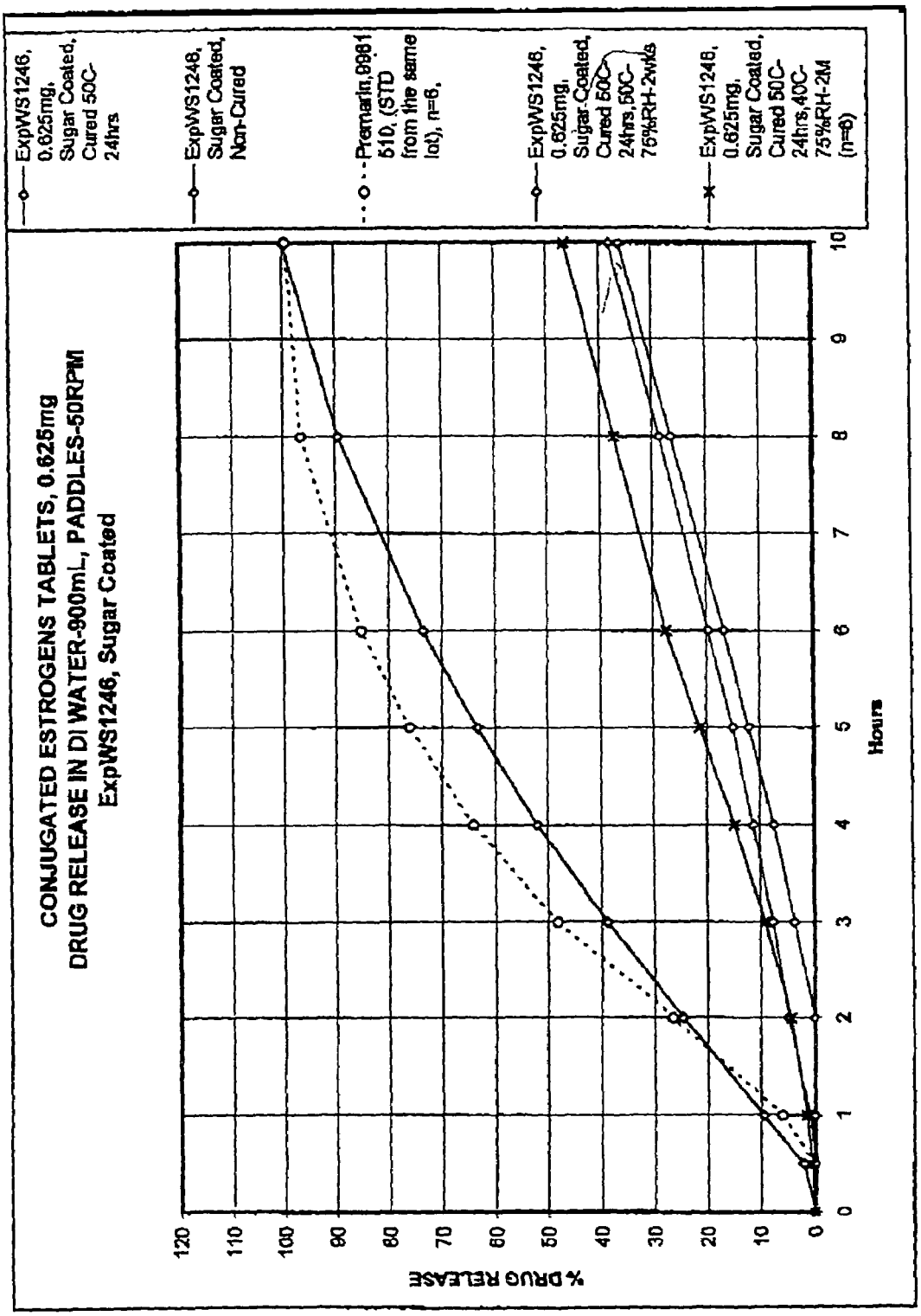
FIG. 1 shows a graphical representation of the comparative drug release results achieved for various sugar coated 0.625 mg dose conjugated estrogen tablets, as compared to a Premarin® tablet as a control.

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

Definitions

In describing and claiming the present invention, the following terminology will be used.

The singular forms "a," "an," and "the" include plural referents unless the context clearly dictates otherwise. Thus, for example, reference to "a polymer" includes reference to one or more types of polymers, and reference to "an estrogen" includes reference to one or more types of estrogen.

The term "formulation" and "composition" may be used interchangeably herein.

The phrases "therapeutically effective amount" refers to an amount of conjugated estrogen sufficient to achieve therapeutic or adequate hormone supplementation results. The determination of an effective amount is well within the ordinary skill in the art of pharmaceutical, cosmetic, and medical sciences. See, for example, Meiner and Tonascia, "Clinical Trials: Design, Conduct, and Analysis," *Monographs in Epidemiology and Biostatistics*, Vol. 8 (1986), incorporated by reference in its entirety.

As used herein, "free of" and "substantially free of" refer to the absence of a specific agent or compound, or if present, such agent or compound is present in an amount that does not provide its functional purpose to a measurable degree. For example, a tablet coating that is "free of," or "substantially free of" a hormone may be either totally hormone free, or contain such a minute amount of hormone, so as to provide no measurable physiological effect. In some cases, the phrase "completely free of" may be used to indicate the complete and total absence of a specific agent or compound.

The term "administration" refers to oral delivery of conjugated estrogen. This method and other methods of administration are well known to those in the pharmaceutical arts.

The term "cellulose" refers to a polysaccharide consisting of anhydroglucose units joined by an oxygen linkage to form long molecular chains that are essentially linear. A number of specific cellulose inclusive compounds are known and used as excipients in the pharmaceutical arts, including without limitation, hydroxypropylmethylcellulose, hydroxypropylcellulose, hydroxyethylcellulose, hydroxybutylethylcellulose, hydroxybutylmethylcellulose, ethylcellulose, carboxymethylcellulose, sodium carboxymethylcellulose, as well as other cellulose derivatives. As such, the recitation of the term "cellulose" generically, should be interpreted to include such specific cellulosic compounds, as well as others not expressly recited.

The term "sugar" refers to any type of simple carbohydrate, such as a mono or disaccharide, or a combination thereof, either naturally obtained, refined from a natural source, or artificially produced. A variety of sugars are known and used in various pharmaceutical formulations, including without limitation, sucrose, glucose, mannose, fructose, lactose, etc. As such, the recitation of the term "sugar" generically, should be interpreted to include such specific compounds, as well as others not expressly recited.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited.

As an illustration, a concentration range of "about 1% w/w to about 10% w/w" should be interpreted to include not only the explicitly recited concentration of about 1% to about 10% w/w, but also include individual concentrations and the sub-ranges within the indicated range. Thus, included in this numerical range are individual concentrations such as 2% w/w, 5% w/w, and 8% w/w, and sub-ranges such as from 1% w/w to 3% w/w, from 2% w/w to 4% w/w, from 3% w/w to 8% w/w, from 5% w/w to 9% w/w, from 1% w/w to 7% w/w etc. The same principle applies to ranges reciting only one numerical value.

Similarly, an open ended range recited as "less than about 10% w/w" should be interpreted to include all of the values and ranges as elaborated above for the range of "from about 1% w/w to about 10% w/w." Furthermore, it is understood that functional limitations may exist for limits not expressly recited by an open ended range, and that such limitations are inherently included as part of the disclosure of the present application, though not expressly recited. Such an interpretation should apply regardless of the breadth of the range or the characteristics being described.

Invention

The present invention relates to a formulation comprising a core containing conjugated estrogens, one or more inorganic excipients, one or more organic excipients, and one or more fillers, and a coating comprising either a sugar or one or more acrylic polymers and/or copolymers. The oral dosage formulation of the present invention includes in one aspect, a tablet having a core and a coating. The tablet may be made in accordance with a variety of techniques known to those skilled in the pharmaceutical arts. For example, the core may contain a simple admixture of particulate, or beaded ingredients, as is known, or beads may be provided that have specific configurations, such as an inner center of excipient, surrounded by a conjugated estrogen. Other possible core configurations will be readily recognized by those skilled in the art.

The conjugated estrogens of the present invention are those generally known and described in the art as conjugated estrogens. See United States Pharmacopia (USP 23). While conjugated estrogens are typically a mixture of estrogenic components, such as estrone and equilin, the present invention may be formulated to either utilize such a mixture, or to include only selected or individual estrogenic components. These conjugated estrogens may be of synthetic or natural origin. Naturally occurring conjugated estrogens are obtained from pregnant mare urine and then are processed and may be stabilized. Examples of such processes are set forth in U.S. Pat. Nos. 2,565,115 and 2,720,483, each of which are incorporated herein by reference. Many conjugated estrogen products are now commercially available.

Conjugated estrogens are also made synthetically. Examples of synthetically produced estrogens include estropipate and ethinyl estradiol. "Conjugated estrogens" as used herein includes both natural and synthetic conjugated estrogens, such as the Pharmacopia inclusive compounds alluded to above, as well as other estrogens so considered by those skilled in the art. Further, "conjugated estrogens" refers to esters of such compounds, such as the sulfate esters, salts of such compounds, such as sodium salts, and esters of the salts of such compounds, such as sodium salts of a sulfate ester, as well as other derivatives known in the art. Some specific examples include: 17-alpha and beta-dihydroequilin, equilenin, 17-alpha and beta-dihydroequilenin, estrone, 17-beta-estradiol, and their sodium sulfate esters.

The specific conjugated estrogen dose included in the tablet of the present invention may be any dosage required to achieve a specific therapeutic effect, and may vary depending on the specific treatment indicated, and on the specific conjugated estrogen included in the tablet. However, in general, dosages of conjugated estrogens included in the tablet, can range from about 0.2 mg/tablet to about 3.0 mg/tablet.

In addition, the present dosage forms can include other hormones such as progestins and androgens. Such hormones may be incorporated either into the core or coating of the present tablet, as discussed further below. Specific progestins that may be used include without limitation: progesterone, medroxyprogesterone, and a variety of synthetic progestins and their salts, esters, and derivatives that are generally known and used in the oral contraceptive area. Specific androgens that may be used, include without limitation, testosterone, methyltestosterone, and other known derivatives and their esters and salts, including deconoate, cypionate, propionate, etc. Any of these hormones can also be micronized.

The inorganic excipients include calcium phosphate tribasic, and calcium carbonate. The calcium phosphate tribasic is present at less than about 20% of the weight of the composition. In some aspects, the calcium phosphate tribasic is present at less than about 15% by weight; in some aspects, less than about 10% by weight; in some aspects, it is less than 8% by weight; and in some aspects, it is less than 5% by weight of the composition. In another aspect, the calcium phosphate tribasic ingredient may be present in an amount of from about 0.5% by weight to about 20% by weight. In one aspect, it has been discovered that when the calcium phosphate tribasic is present at these proportions, the physical stability of the composition is greatly increased during storage, for example by reduced cracking, as compared to those compositions of U.S. Pat. No. 5,908,638.

The invention also comprises one or more organic excipients in the tablet core, such as a cellulose ingredient. In one aspect, the cellulose may be hydroxypropylmethylcellulose. Other excipients that can be used in the core of the composition include without limitation: hydroxypropyl cellulose, carboxymethylcellulose, ethyl cellulose, methyl cellulose, their derivatives and salts, as well as mixtures thereof. Additionally, other organic excipients, such as polyethylene glycol, talc, lactose, starch, sorbitol, mannitol, polyvinylpyrolidone can also be used.

In one particular aspect, lactose, or another sugar may be included in the core, wherein the lactose, or other sugar is present at less than about 50% by weight of the formulation. In one aspect, the lactose, or other sugar may be present in an amount of from about 1% to about 50% by weight. In some aspects, the amount may be from about 10% to about 50% by weight; in some aspects, from about 10% to about 40%; in some other aspects, from about 10% to about 30% by weight; in yet other aspects, from about 5% to about 30% by weight; in yet some other aspects, from about 5% to about 50% by weight. In one aspect, the amount may be from about 20% to about 30% by weight.

Notwithstanding the above-recited core ingredients and amounts therefore, in one aspect, the tablet of the present invention may include gel forming excipients, such as various celluloses and gelatins, in an amount of less than about 25% w/w of the composition. In use, such excipients form a gel in an aqueous solution, and therefore, when the tablet coating is penetrated by digestive fluids, the core swells and ruptures the coating to facilitate release of the conjugated estrogen. In another aspect of the invention, the amount of gel forming excipients may be less than about 20% w/w of the composition. In yet another aspect, the amount may be less than about 15% w/w of the composition. In a further aspect, the amount may be from about 1%-25% w/w.

The coating for the tablet of the present invention may be made from a wide variety of materials including sugars and acrylic polymers and copolymers. Of particular note is that in one aspect, no hormones are contained in the coating. In other aspects, the coating may contain hormones in addition to a variety of other ingredients known to those skilled in the art, such as plasticizers, colorants, and solvents or other vehicles. Notably, such ingredients create a barrier that is initially soluble in gastrointestinal fluid, in order to achieve an initial drug release. By contrast, many sustained release formulations, such as the formulation disclosed in U.S. Pat. No. 5,908,638 require that the tablet coating provide a coating that is impervious to stomach fluid for at least the first few hours. As such, in one aspect, the tablet of the present invention may include a coating that provides initial drug release while in the stomach of a subject. In another aspect, initial drug release may occur in less than about 2 hours after administration. In yet another aspect, initial drug release may occur in less than about 1 hour after administration.

A wide variety of sugars may be used for the coating of the present invention as known to those skilled in the art. Examples of suitable sugars include without limitation, sucrose derived from a variety of sources, such as beet or cane sources, starch, saccharide or polysaccharide converted sources, and which is considered suitable for use in pharmaceutical applications.

A number of acrylic polymers or copolymers known to those skilled in the art may also be used to form the coating of the tablet of the present invention. Examples of specific polymers include without limitation, polymers of acrylic esters, such as methacrylate, and methyl methacrylate copolymers. Various acceptable polymers may be obtained from a variety of commercial sources, such as EUDRAGIT® polymers available from Rohm and Haas Corporation. In one aspect, the coating may include a mixture or blend of acrylic polymers or copolymers. In another aspect, the mixture may be present at a ratio of from about 1:10 to about 10:1. In a further aspect, the ratio may be from about 1:5 to 5:1. In yet another aspect, the ratio may be from about 1:2 to about 2:1.

The present invention is distinct from the previously known and/or disclosed formulations in at least the following ways:

a) in the presence of lactose or similar sugar excipient in an amount of about or less than 50% by weight; or from about 1%-50% by weight; or from about 5%-50% by weight, or from about 10%-40% by weight, or from about 10%-30% by weight; or from about 20%-30% by weight;

b) in the presence of calcium phosphate tribasic in an amount of less than 20% by weight; or from about 0.5%-20% by weight; or from about 5%-20% by weight; or from about 5%-15% by weight; or from about 1%-15% by weight; or from about 1%-10% by weight; or from about 5%-10% by weight;

c) in the absence of a substantial amount of a hormone in the outer coating layer in some embodiments;

d) in the absence of a substantial amount of a microcrystalline cellulose in the outer coating layer to aid in controlling the release of the drug from the core;

e) in the absence of a substantial amount of a moisture barrier imparting polymer (i.e. ethyl cellulose) as an outer coat that prevents dissolution in the gastrointestinal fluid of the stomach, and therefore prevents of minimizes drug release in the stomach; and f) in the presence of gel forming excipients in an amount of less than about 25% w/w of the composition; 20% w/w of the composition, 15% w/w, or from about 1% w/w to about 25% w/w of the composition.

It has been discovered that when the composition for conjugated estrogens comprises the above distinct characteristics, the composition does not crack over long storage times, provides a drug release that is very comparable to the commercially successful product known an Premarin®, and yet is simple to prepare. The prior known or disclosed compositions, although used commercially, have lacked one or more of the above characteristics and therefore have the need to be improved for optimal stability and patient acceptance.

More specifically, U.S. Pat. No. 5,547,948 discloses a core comprising conjugated estrogens and excipients and a sugar coat that also comprises a hormone and microcrystalline cellulose to control the release of the hormone from the coating. The invention in the '948 patent is directed at delivering the hormone in the sugar coating, and does not teach or suggest compositions that deliver conjugated estrogens from the core wherein such compositions comprise inorganic excipients such as calcium phosphate tribasic and yet that do not crack. In contrast, the present invention does not comprise a sugar coating that controls the release of the hormone.

U.S. Pat. No. 5,395,627 teaches hormonal dosage forms wherein the core is made up of desogestrel, ethinylestradiol, and lactose and polyvinylpyrrolidone, among others, and a film coat comprising HPMC and PEG. The specification teaches diluents such as lactose from about 70% to about 95% by weight of the composition and does not teach the inclusion of conjugated estrogens. In contrast, the excipients of the present invention comprise lactose at about or less than about 50% by weight and contain an inorganic excipient such as calcium phosphate tribasic and comprise conjugated estrogens.

U.S. Pat. No. 5,720,977 teaches formulations comprising estropipate, calcium glycerophosphate, citric acid, and sodium bicarbonate to provide effervescence. Estropipate, which can also be used in the present invention, is admittedly distinct from naturally occurring conjugated estrogens in that the latter are highly moisture sensitive, whereas estropipate is known to be "stable." See, column 3, lines 17-25.

U.S. Pat. No. 5,908,638 teaches that in order to accomplish stable conjugated estrogen formulations: a) the moisture content must be less than 2.5% free water; b) inorganic excipients should not be present; c) shellac coating should be avoided; c) the core tablets must be coated using a moisture barrier material. See, columns 7, 8, 10, and 14. This patent teaches that water bound to organic excipients do not cause any deleterious effects to the conjugated estrogens. See column 8, lines 39-41.

In contrast to these teachings, the present invention comprises an inorganic excipient, in some embodiments a shellac coating, and does not contain a moisture barrier coating. Rather, only a sugar coating or an acrylic coating is used. Further, it is believed, without wishing to be bound by any theory, that the particular combination of one or more of the above unique characteristics result in conjugated estrogen formulations that deliver the drug at rates comparable to the commercially successful Premarin® formulation. Further, such a formulation is stable and does not crack on extended storage, such as for one month, or two months or longer, under accelerated stability temperature and humidity conditions. Or, of a more practical nature, as indicated by passing accelerated stability tests, the compositions of the present invention are stable and do not crack over an extended period of time under ambient conditions of temperature and humidity as found in various environments.

One contributing factor to the success of the present inventions may be, again without wishing to be bound by any theory, the presence of lactose in lower amounts (i.e., at about or less than 50% by weight and other amounts disclosed herein) than in the previously disclosed formulations of conjugated estrogens. Another contributing factor may be, again without wishing to be bound by any theory, the presence of low amounts (less than or about 20% by weight or other amounts as disclosed herein) of calcium compound such as calcium phosphate tribasic. It is also possible that one or more of these factors taken either alone, or in combination contribute to the desired physical characteristics described above.

A variety of conventional methods known to those skilled in the art may be used to produce the tablets of the present invention. Examples of such methods, such as wet granulation, fluid-bed granulation, dry granulation, and direct compression may be found in *Remmington's Pharmaceutical Sciences* pp. 1615-1649 (19$^{th}$ ed. 1995).

EXAMPLE 1

The active bulk ingredients were weighed and comminuted with hydroxypropylmethyl cellulose (Methocel K-3) under nitrogen atmosphere. The mixture was passed through a #20 mesh screen. The resulting mixture was blended with dehydrated alcohol under nitrogen atmosphere and dried with a loss on drying no greater than 2.5%. The dried mixture was then again passed through a Mesh #20 screen. The mixture was then blended with calcium phosphate tribasic, lactose (Fast-flo316) and microcrystalline cellulose (Avicel PH 113), again under nitrogen atmosphere. This mixture was further treated with stearic acid and magnesium stearate as lubricants. The resulting blend was dried again with a loss on drying no more than 2.5%. The dried mixture was then compressed into tablets on a rotary tablet press.

EXAMPLE 2

Tablets prepared as in Example 1, and having a core composition as shown in Table 1, were placed in a 24" Accelacota Side Vented coating pan and coated with shellac. This was followed by a coating of sugar. The resulting sugar-coated tablets were cured for 24 hours in a Nary oven at 50° C. The composition of the sugar-coated tablets is given in the following Table 1.

TABLE 1

Composition of sugar-coated 0.625 mg conjugated estrogens tablets

| Ingredient | Mg/tablet |
|---|---|
| CORE | |
| Conjugated estrogens | 0.625 |
| Methocel K-3 Prem. LV | 40.0 |
| Lactose (Fast-flo316) | 55.5 |
| Calcium Phosphate Tribasic, USP | 7.0 |
| Avicel PH 113 | 26.0 |
| Stearic Acid | 0.65 |
| Magnesium Stearate NF | 0.65 |
| #4 Refined Pharmaceutical Glaze, NF in 45/200 Alcohol | 7.2 (solid) |
| Talc, USP (Alphafil 500) | 7.2 |
| COATING | |
| Sucrose, NF | 111.3 |
| Calcium Sulfate, NF | 6.23 |
| Talc, USP | 2.25 |
| PEG 8000, USP | 0.09 |
| Carnuba Wax, NF | 0.15 |
| Total | 264.8 mg/tablet |

EXAMPLE 3

Tablets as prepared in Example 1, and having the core composition as in Table 2, were placed in a 24" Accelacota Side Vented coating pan and coated with methacrylic acid copolymers. Such copolymers are commercially known as Eudragit RL30D and Eudragit RS30D. The resulting acrylic-coated tablets were cured for 24 hours in a Nary oven at 50° C. The composition for the acrylic coated tablets is given in the following Table 2.

TABLE 2

Composition of acrylic-coated 0.625 mg conjugated estrogens tablets

| Ingredient | Mg/tablet |
|---|---|
| CORE | |
| Conjugated estrogens | 0.625 |
| Methocel K-3 Prem. LV | 40.0 |
| Lactose (Fast-flo316) | 55.5 |
| Calcium Phosphate Tribasic, USP | 6.5 |
| Avicel PH 113 | 26.0 |
| Stearic Acid | 0.65 |
| Magnesium Stearate NF | 0.65 |
| Talc, USP (Alphafil 500) | 5.35 |
| COATING | |
| Eudragit RS-30D | 4.88 (solid) |
| Eudragit RL-30D | 2.44 (solid) |
| Triethyl citrate | 0.33 |
| Antifoam | 0.70 |
| Opadryl, Clear (YS-1-10925-A) | 1.3 |
| Total | 144.9 mg/tablet |

EXAMPLE 4

Stability and drug release rates were studied for sugar-coated tablets as prepared in Example 1 and Table 1. Stability was monitored under different storage conditions. These conditions included: 50° C., 75% relative humidity, after two weeks; 40° C., 75% relative humidity, after one month; 40° C., 75% relative humidity, after two months. The samples were monitored for various active compounds and degradation products as specified in the USP. The data are shown in Table 3. These data indicate that the sugar-coated tablets of the present invention were stable under all these accelerated conditions. This is established by the fact that the various active compounds and the degradation products were within the specified limits for USP.

TABLE 3

0.625 mg Coated (Sugar) Tablets

Conjugated Estrogens-Stability Studies
Product: 0.625 mg Coated Tablets
Lot # EXPWS 1246
Coating R&D s/n

| | | 001659 | 001752 | | 002163 | | 002300 | |
|---|---|---|---|---|---|---|---|---|
| | | | Storage Condition | | | | | |
| | | Initial | 50c, 75% RH/2 wks | | 40c, 75% RH/1 mnth | | 40c, 75% RH/2 mnth | |
| | USP limits | % Found | % Found | % Initial | % Found | % Initial | % Found | % Initial |
| Estrone | 52.5-61.5% | 49.1 | 50.8 | 103.5 | 50.2 | 102.2 | 50.2 | 102.2 |
| Equilin | 22.5-30.5% | 22.7 | 23.3 | 102.6 | 23.0 | 101.3 | 23 | 101.3 |
| Estrone + Equilin | 79.5-88.0% | 71.8 | 74.0 | 103.1 | 73.2 | 101.9 | 73.2 | 101.9 |
| 17a-dihydroequilin | 13.5-19.5% | 14.0 | 14.5 | 103.6 | 14.3 | 102.1 | 14.5 | 103.6 |
| 17a-estradiol | 2.5-9.5% | 3.8 | 3.8 | 100.0 | 3.9 | 102.6 | 3.9 | 102.6 |
| 17b-estradiol | <2.25% | 0.60 | 0.59 | 98.3 | 0.56 | 93.3 | 0.62 | 103.3 |

TABLE 3-continued 0.625 mg Coated (Sugar) Tablets

Conjugated Estrogens-Stability Studies  
Product: 0.625 mg Coated Tablets  
Lot #                EXPWS 1246  
Coating

|  |  | R&D s/n | | | | | | |
|---|---|---|---|---|---|---|---|---|
|  |  | 001659 | 001752 | | 002163 | | 002300 | |
|  |  | | | Storage Condition | | | | |
|  |  | Initial | 50c, 75% RH/2 wks | | 40c, 75% RH/1 mnth | | 40c, 75% RH/2 mnth | |
|  | USP limits | % Found | % Found | % Initial | % Found | % Initial | % Found | % Initial |
| 17b-dihydroequilin | 0.5-4.0% | 1.3 | 1.3 | 100.0 | 1.3 | 100.0 | 1.4 | 107.7 |
| 17a-dihydroequilenin | <3.25% | 2.05 | 2.19 | 106.8 | 2.16 | 105.4 | 2.2 | 107.3 |
| 17b-dihydroequilenin | <2.75% | 0.56 | 0.63 | 112.5 | 0.58 | 103.6 | 0.44 | 78.6 |
| d8,9 dehydroesterone | <6.25% | 4.72 | 4.91 | 104.0 | 4.68 | 99.2 | 4.53 | 96.0 |
| Equilenin | <5.5% | 2.6 | 2.8 | 107.7 | 2.8 | 107.7 | 2.8 | 107.7 |
| Equilin/Estrone | 0.35-0.65% | 0.46 | 0.48 | 100.0 | 0.46 | 100.0 | 0.46 | 99.7 |
| LOD % |  |  | 1.15 | 1.79 |  | 1.55 |  | 1.33 |

EXAMPLE 5

Stability and drug release rates were studied for acrylic-coated tablets made in accordance with Example 1 and Table 2. Stability was monitored under different storage conditions. These conditions included: 50° C., 75% relative humidity, after two weeks; 40° C., 75% relative humidity, after one month; 40° C., 75% relative humidity, after two months. The samples were monitored for various active compounds and degradation products as specified in the USP. The data are shown in Table 4. These data indicate that the acrylic-coated tablets of the present invention were stable under all these accelerated conditions. This is established by the fact that the various active compounds and the degradation products were within the specified limits for USP.

TABLE 4

0.625 mg Coated (acrylic) Tablets

Conjugated Estrogens-Stability Studies  
Product: 0.625 mg Coated Tablets  
Lot #                EXPWS 1251  
Coating              10% Eudragit/RS:RL (2:1)

|  |  | R&D s/n | | | | | | | | | |
|---|---|---|---|---|---|---|---|---|---|---|---|
|  |  | 001560 | 01656 | | 001767 | | 020874 | | 002298 | | |
|  |  | | | | | Storage Condition | | | | | |
|  |  | Initial | 50c, 75% RH/2 wks | | 40c, 75% RH/1m | | 40c, 75% RH/2m | | 40c, 75% RH/3m | | |
|  | USP limits | % Found | % Found | % Initial | % Found | % Initial | % Found | % Initial | % Found | % Initial | Change |
| Estrone | 52.5-61.5% | 55.9 | 55.2 | 98.7 | 56.6 | 101.3 | 55.9 | 100.00 | 56.4 | 100.9 | 0.5 |
| Equilin | 22.5-30.5% | 27.3 | 26.5 | 97.1 | 27.1 | 99.3 | 26.5 | 97.1 | 26.4 | 96.7 | 0.9 |
| Estrone + Equilin | 79.5-88.0% | 83.2 | 81.7 | 96.2 | 83.6 | 100.5 | 82.4 | 99.0 | 82.9 | 99.6 | 0.3 |
| 17a-dihydroequilin | 13.5-19.5% | 17.9 | 17.4 | 97.2 | 17.9 | 100.0 | 17.6 | 98.3 | 18.1 | 101.1 | -0.2 |
| 17a-estradiol | 2.5-9.5% | 4.6 | 4.5 | 97.8 | 4.7 | 102.2 | 4.7 | 102.2 | 4.8 | 104.3 | -0.2 |
| 17b-estradiol | <2.25% | 1.26 | 1.11 | 88.1 | 0.90 | 71.4 | 0.96 | 76.2 | 0.88 | 69.8 | 0.38 |
| 17b-dihydroequilin | 0.5-4.0% | 2.3 | 2.2 | 95.7 | 2.6 | 108.7 | 2.4 | 104.3 | 2.4 | 104.3 | -0.1 |
| 17a-dihydroequilenin | <3.25% | 1.65 | 1.79 | 108.5 | 2.03 | 123.0 | 2.34 | 141.8 | 2.82 | 170.9 | -1.17 |
| 17b-dihydroequilenin | <2.75% | 0.77 | 0.67 | 87.0 | 0.97 | 126.0 | 0.86 | 111.7 | 0.68 | 88.3 | 0.09 |
| d8,9 dehydroesterone | <6.25% | 4.15 | 4.07 | 98.1 | 4.13 | 99.5 | 4.02 | 96.9 | 3.91 | 94.2 | 0.24 |
| Equilenin | <5.5% | 2.2 | 2.5 | 113.6 | 2.3 | 104.5 | 2.6 | 118.2 | 3.0 | 136.4 | -0.8 |
| Equilin/Estrone | 0.35-0.65% | 0.49 | 0.48 | 98.0 | 0.48 | 97.6 | 0.47 | 96.7 | 0.47 | 95.6 | 0.02 |
| LOD % |  |  | 2.52 | 2.35 |  | 2.94 |  | 3.04 |  | 3.18 |  |

EXAMPLE 6

The drug release profile was obtained for the sugar-coated conjugated estrogen tablets of the present invention. Standard USP methodology was followed, which included using distilled water (900 ml), paddles at 50 rpm. The data were displayed graphically as shown in FIG. 1. A positive control of Premarin® was used to validate further the data.

These data indicate that at least some sugar-coated tablets of the present invention release under some conditions the conjugated estrogens at approximately the same rate as the Premarin® product.

EXAMPLE 7

Figure 2:
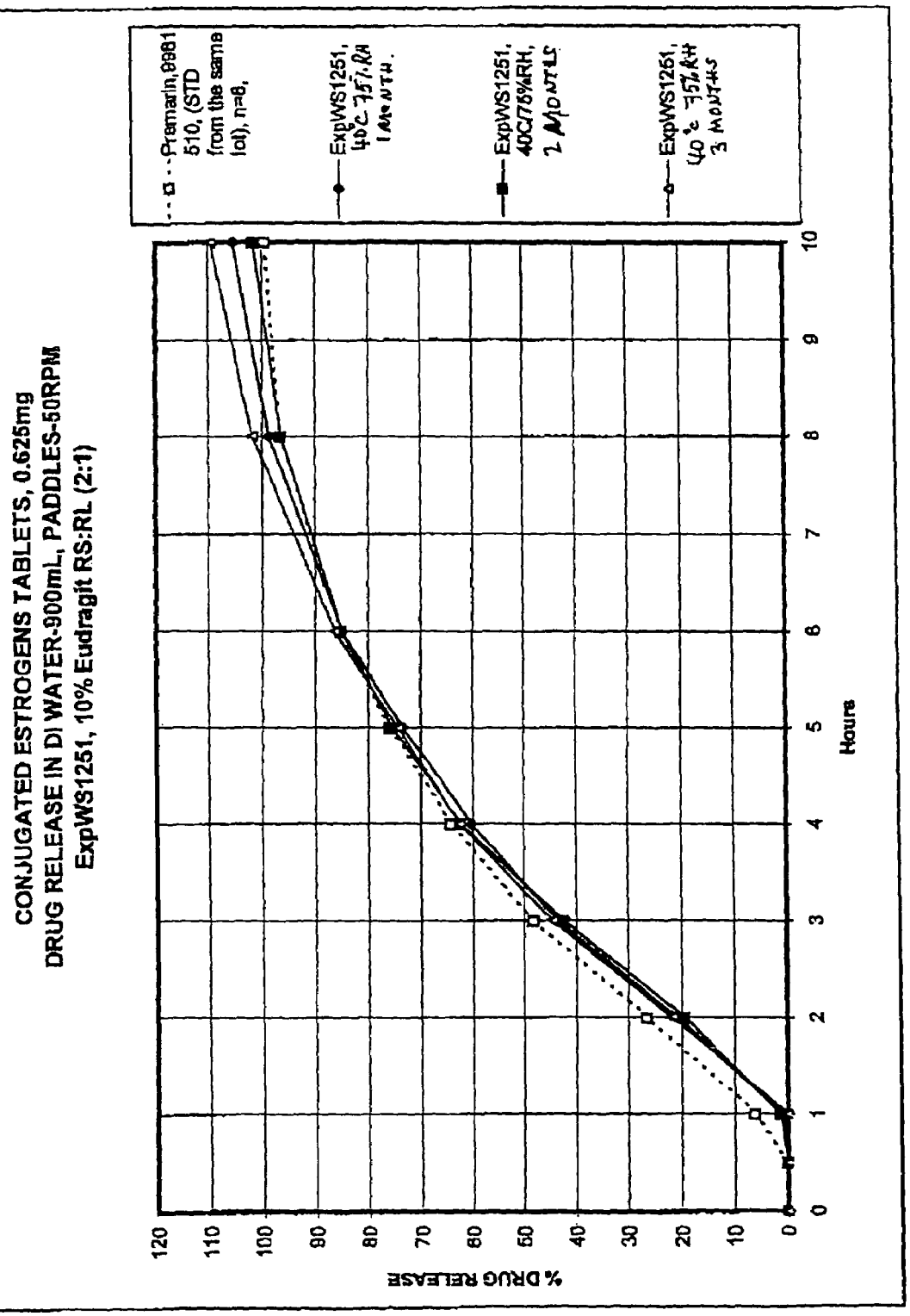
FIG. 2 shows a graphical representation of the comparative drug release results achieved for various acrylic coated 0.625 mg dose conjugated estrogen tablets, as compared to a Premarin® tablet as a control.

The drug release profile was obtained for the acrylic-coated conjugated estrogen tablets of the present invention. Standard USP methodology was followed, which included using distilled water (900 ml), paddles at 50 rpm. The data were displayed graphically as shown in FIG. 2. A positive control of Premarin® was used to validate further the data.

These data indicate that acrylic-coated tablets of the present invention release the conjugated estrogens at approximately the same rate as the Premarin product®. This release rate is noted to be closer for all conditions tested.

Of course, it is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A pharmaceutical composition in a solid oral dosage form comprising:
   a core containing a therapeutically effective amount of at least one conjugated estrogen, or a component thereof, and at least one organic excipient, wherein the at least one organic excipient comprises less than about 25% w/w of a cellulose ingredient, and less than about 50% w/w of a sugar ingredient, and at least one inorganic excipient, wherein the at least one inorganic excipient comprises a calcium phosphate tribasic ingredient in an amount of less than about 20% w/w; and
   a pharmaceutically acceptable coating that is free of hormones, wherein the composition does not crack when stored at 40° C. and 75% relative humidity for about two months.

2. The pharmaceutical composition of claim 1, wherein the therapeutically effective amount of conjugated estrogen is from about 0.1 mg to about 3 mg.

3. The pharmaceutical composition of claim 2, wherein the amount is about 0.625 mg.

4. The pharmaceutical composition of claim 1, wherein the coating is a sugar coating.

5. The pharmaceutical composition of claim 1, wherein the coating is an acrylic coating.

6. The pharmaceutical composition of claim 1, wherein the sugar ingredient is present in an amount of from about 5% w/w to about 50% w/w.

7. The pharmaceutical composition of claim 1, wherein the sugar ingredient is present in an amount of from about 10% w/w to about 40% w/w.

8. The pharmaceutical composition of claim 1, wherein the sugar ingredient is present in an amount of from about 20% w/w to about 30% w/w.

9. The pharmaceutical composition of claim 1, wherein the calcium phosphate tribasic ingredient is present in amount of from about 1% w/w to about 15% w/w.

10. The pharmaceutical composition of claim 1, wherein the calcium phosphate tribasic ingredient is present in amount of from about 5% w/w to about 15% w/w.

11. The pharmaceutical composition of claim 1, wherein the calcium phosphate tribasic ingredient is present in amount of from about 1% w/w to about 10% w/w.

12. The pharmaceutical composition of claim 1, wherein the calcium phosphate tribasic ingredient is present in an amount of from about 5% w/w to about 10% w/w.

13. The pharmaceutical composition of claim 1, wherein the conjugated estrogen is of a natural origin.

14. The pharmaceutical composition of claim 1, wherein the conjugated estrogen is of a synthetic origin.

15. The pharmaceutical composition of claim 1, wherein the conjugated estrogen is a mixture of estrogenic components.

16. The pharmaceutical composition of claim 1, wherein the conjugated estrogen is an ester of an estrogen.

17. The pharmaceutical composition of claim 1, wherein the cellulose ingredient is a member selected from the group consisting of: hydroxypropyl cellulose, carboxymethylcellulose, ethyl cellulose, methyl cellulose, salts thereof, derivatives thereof, and mixtures thereof.

18. The pharmaceutical composition of claim 17, wherein the cellulose ingredient is hydroxypropyl cellulose.

19. The pharmaceutical composition of claim 1, wherein the sugar ingredient is a member selected from the group consisting of: sucrose, glucose, mannose, fructose, lactose, and mixtures thereof.

20. The pharmaceutical composition of claim 19, wherein the sugar ingredient is sucrose.

21. The pharmaceutical composition of claim 20, wherein the sucrose is derived from a source selected from the group consisting of: beet sources, cane sources, starch, saccharide converted sources, polysaccharide converted sources, and mixtures thereof.

22. The pharmaceutical composition of claim 21, wherein the sucrose is derived from cane sources.

* * * * *